United States Patent
Zhang

(10) Patent No.: US 10,244,957 B2
(45) Date of Patent: Apr. 2, 2019

(54) METHOD AND APPARATUS FOR SELECTING A SENSING VECTOR CONFIGURATION IN A MEDICAL DEVICE

(71) Applicant: Medtronic, Inc., Minneapolis, MN (US)

(72) Inventor: Xusheng Zhang, Shoreview, MN (US)

(73) Assignee: Medtronic, Inc., Minneapolis, MN (US)

(*) Notice: Subject to any disclaimer, the term of this patent is extended or adjusted under 35 U.S.C. 154(b) by 0 days.

(21) Appl. No.: 14/339,980

(22) Filed: Jul. 24, 2014

(65) Prior Publication Data
US 2015/0305638 A1    Oct. 29, 2015

Related U.S. Application Data

(60) Provisional application No. 61/983,499, filed on Apr. 24, 2014.

(51) Int. Cl.
| | |
|---|---|
| *A61B 5/04* | (2006.01) |
| *A61B 5/0408* | (2006.01) |
| *A61B 5/00* | (2006.01) |
| *A61B 5/0452* | (2006.01) |
| *A61B 5/0456* | (2006.01) |

(Continued)

(52) U.S. Cl.
CPC ........ *A61B 5/04011* (2013.01); *A61B 5/0408* (2013.01); *A61B 5/0452* (2013.01); *A61B 5/0456* (2013.01); *A61B 5/7221* (2013.01); *A61N 1/3621* (2013.01); *A61N 1/3962* (2013.01)

(58) Field of Classification Search
CPC .................................................. A61B 5/0464
See application file for complete search history.

(56) References Cited

U.S. PATENT DOCUMENTS

| | | |
|---|---|---|
| 4,374,382 A | 2/1983 | Markowitz |
| 4,556,063 A | 12/1985 | Thompson et al. |
| 4,567,892 A | 2/1986 | Plicchi et al. |

(Continued)

FOREIGN PATENT DOCUMENTS

| | | |
|---|---|---|
| AU | 2010201351 | 4/2010 |
| EP | 1615693 | 1/2006 |

(Continued)

OTHER PUBLICATIONS (PCT/US2015/023351) PCT Notification of Transmittal of the International Search Report and the Written Opinion of the International Searching Authority.

(Continued)

*Primary Examiner* — Carl H Layno
*Assistant Examiner* — Jennifer Ghand

(57) ABSTRACT

A method and medical device for determining sensing vectors that includes sensing cardiac signals from a plurality of electrodes, the plurality of electrodes forming a plurality of sensing vectors, determining a sensing vector metric in response to the sensed cardiac signals, determining a morphology metric associated with a morphology of the sensed cardiac signals, determining vector selection metrics in response to the determined sensing vector metric and the determined morphology setting, and selecting a sensing vector of the plurality of sensing vectors in response to the determined vector selection metrics.

21 Claims, 7 Drawing Sheets

(51) Int. Cl.
    *A61N 1/362* (2006.01)
    *A61N 1/39* (2006.01)

(56) References Cited

U.S. PATENT DOCUMENTS

| | | |
|---|---|---|
| 4,870,974 A | 10/1989 | Wang |
| 5,127,404 A | 7/1992 | Wyborny et al. |
| 5,176,137 A | 1/1993 | Erickson et al. |
| 5,191,884 A | 3/1993 | Gilli et al. |
| 5,193,535 A | 3/1993 | Bardy et al. |
| 5,257,621 A | 11/1993 | Bardy et al. |
| 5,312,443 A | 5/1994 | Adams et al. |
| 5,330,508 A | 7/1994 | Gunderson |
| 5,334,966 A | 8/1994 | Takeshima et al. |
| 5,447,519 A | 9/1995 | Peterson |
| 5,464,434 A | 11/1995 | Alt |
| 5,545,186 A | 8/1996 | Olson et al. |
| 5,593,431 A | 1/1997 | Sheldon |
| 5,687,733 A | 11/1997 | McKown |
| 5,720,295 A | 2/1998 | Greenhut et al. |
| 5,755,736 A | 5/1998 | Gillberg et al. |
| 5,755,737 A | 5/1998 | Prieve et al. |
| 5,755,739 A | 5/1998 | Sun et al. |
| 5,782,876 A | 7/1998 | Flammang |
| 5,800,465 A | 9/1998 | Thompson et al. |
| 5,836,975 A | 11/1998 | DeGroot |
| 5,846,263 A | 12/1998 | Peterson et al. |
| 5,855,593 A | 1/1999 | Olson et al. |
| 5,857,977 A | 1/1999 | Caswell et al. |
| 5,893,882 A | 4/1999 | Peterson et al. |
| 5,931,857 A | 8/1999 | Prieve et al. |
| 5,987,356 A | 11/1999 | DeGroot |
| 5,991,656 A | 11/1999 | Olson et al. |
| 6,029,086 A | 2/2000 | Kim et al. |
| 6,052,620 A | 4/2000 | Gillberg et al. |
| 6,115,628 A | 9/2000 | Stadler et al. |
| 6,134,479 A | 10/2000 | Brewer et al. |
| 6,141,581 A | 10/2000 | Olson et al. |
| 6,178,350 B1 | 1/2001 | Olson et al. |
| 6,230,059 B1 | 5/2001 | Duffin |
| 6,236,882 B1 | 5/2001 | Lee et al. |
| 6,259,947 B1 | 7/2001 | Olson et al. |
| 6,287,328 B1 | 9/2001 | Snyder et al. |
| 6,304,773 B1 | 10/2001 | Taylor et al. |
| 6,397,100 B2 | 5/2002 | Stadler et al. |
| 6,418,343 B1 | 7/2002 | Zhang et al. |
| 6,449,503 B1 | 9/2002 | Hsu |
| 6,480,734 B1 | 11/2002 | Zhang et al. |
| 6,487,443 B2 | 11/2002 | Olson et al. |
| 6,618,622 B1 | 9/2003 | Mann et al. |
| 6,718,204 B2 | 4/2004 | DeGroot et al. |
| 6,731,978 B2 | 5/2004 | Olson et al. |
| 6,754,527 B2 | 6/2004 | Stroebel et al. |
| 6,754,528 B2 | 6/2004 | Bardy et al. |
| 6,862,477 B1 | 3/2005 | Mo |
| 6,879,856 B2 | 4/2005 | Stadler et al. |
| 6,892,094 B2 | 5/2005 | Ousdigian et al. |
| 6,925,329 B1 | 8/2005 | Sloman |
| 7,010,347 B2 | 3/2006 | Schecter |
| 7,027,858 B2 | 4/2006 | Cao et al. |
| 7,043,299 B2 | 5/2006 | Erlinger et al. |
| 7,065,410 B2 | 6/2006 | Bardy et al. |
| 7,076,289 B2 | 7/2006 | Sarkar et al. |
| 7,103,405 B2 | 9/2006 | Sarkar et al. |
| 7,103,464 B2 | 9/2006 | Zielke |
| 7,130,677 B2 | 10/2006 | Brown et al. |
| 7,149,577 B2 | 12/2006 | Sharma et al. |
| 7,151,962 B2 | 12/2006 | Belk |
| 7,184,831 B2 | 2/2007 | Belk |
| 7,194,302 B2 | 3/2007 | Bardy et al. |
| 7,239,925 B2 | 7/2007 | Bardy et al. |
| 7,248,921 B2 | 7/2007 | Palreddy et al. |
| 7,251,757 B2 | 7/2007 | Ouellette et al. |
| 7,274,962 B2 | 9/2007 | Bardy et al. |
| 7,299,092 B2 | 11/2007 | Bardy et al. |
| 7,299,097 B2 | 11/2007 | Bardy et al. |
| 7,317,942 B2 | 1/2008 | Brown |
| 7,330,757 B2 | 2/2008 | Ostroff et al. |
| 7,376,458 B2 | 5/2008 | Palreddy et al. |
| 7,379,772 B2 | 5/2008 | Bardy et al. |
| 7,392,082 B2 | 6/2008 | Sharma |
| 7,392,085 B2 | 6/2008 | Warren et al. |
| 7,406,350 B2 | 7/2008 | Erlinger et al. |
| 7,444,182 B2 | 10/2008 | Ostroff et al. |
| 7,477,935 B2 | 1/2009 | Palreddy et al. |
| 7,583,579 B2 | 9/2009 | Ueki |
| 7,623,909 B2 | 11/2009 | Sanghera et al. |
| 7,623,913 B2 | 11/2009 | Phillips |
| 7,627,367 B2 | 12/2009 | Warren et al. |
| 7,657,322 B2 | 2/2010 | Bardy et al. |
| 7,728,579 B2 | 6/2010 | Mueller |
| 7,734,333 B2 | 6/2010 | Ghanem et al. |
| 7,734,336 B2 | 6/2010 | Ghanem et al. |
| 7,742,812 B2 | 6/2010 | Ghanem et al. |
| 7,761,142 B2 | 7/2010 | Ghanem et al. |
| 7,761,150 B2 | 7/2010 | Ghanem et al. |
| 7,769,452 B2 | 8/2010 | Ghanem et al. |
| 7,774,049 B2 | 8/2010 | Ghanem et al. |
| 7,774,616 B2 | 8/2010 | Dale et al. |
| 7,783,340 B2 | 8/2010 | Sanghera et al. |
| 7,894,894 B2 | 2/2011 | Stadler et al. |
| 7,904,153 B2 | 3/2011 | Greenhut et al. |
| 7,907,993 B2 | 3/2011 | Ghanem et al. |
| 7,930,024 B2 | 4/2011 | Ousdigian |
| 7,937,135 B2 | 5/2011 | Ghanem et al. |
| 7,941,214 B2 | 5/2011 | Kleckner et al. |
| 7,953,489 B2 | 5/2011 | Warren et al. |
| 7,991,459 B2 | 8/2011 | Palreddy et al. |
| 7,991,471 B2 | 8/2011 | Ghanem et al. |
| 7,996,082 B2 | 8/2011 | Palreddy et al. |
| 8,014,851 B2 | 9/2011 | Ostroff et al. |
| 8,027,720 B2 | 9/2011 | Bardy et al. |
| 8,027,791 B2 | 9/2011 | Soykan |
| 8,050,754 B2 | 11/2011 | Ostroff et al. |
| 8,068,901 B2 | 11/2011 | Ghanem et al. |
| 8,073,532 B2 | 12/2011 | Palreddy et al. |
| 8,095,206 B2 | 1/2012 | Ghanem et al. |
| 8,116,867 B2 | 2/2012 | Ostroff |
| 8,160,684 B2 | 4/2012 | Ghanem et al. |
| 8,160,686 B2 | 4/2012 | Allavatam et al. |
| 8,160,687 B2 | 4/2012 | Warren et al. |
| 8,160,697 B2 | 4/2012 | Warren et al. |
| 8,170,663 B2 | 5/2012 | DeGroot et al. |
| 8,185,198 B2 | 5/2012 | Palreddy et al. |
| 8,200,341 B2 | 6/2012 | Sanghera et al. |
| 8,229,563 B2 | 7/2012 | Warren et al. |
| 8,249,702 B2 | 8/2012 | Warren et al. |
| 8,265,737 B2 | 9/2012 | Warren et al. |
| 8,265,749 B2 | 9/2012 | Allavatam et al. |
| 8,285,375 B2 | 10/2012 | Bardy et al. |
| 8,306,618 B2 | 11/2012 | Ghanem et al. |
| 8,332,022 B2 | 12/2012 | Brown et al. |
| 8,346,357 B2 | 1/2013 | Palreddy et al. |
| 8,364,251 B2 | 1/2013 | Phillips |
| 8,435,185 B2 | 5/2013 | Ghanem et al. |
| 8,437,838 B2 | 5/2013 | Warren et al. |
| 8,457,737 B2 | 6/2013 | Bardy et al. |
| 8,483,813 B2 | 7/2013 | Zhang et al. |
| 8,483,843 B2 | 7/2013 | Sanghera et al. |
| 8,494,630 B2 | 7/2013 | Palreddy et al. |
| 8,548,573 B2 | 7/2013 | Keefe |
| 8,565,878 B2 | 10/2013 | Allavatam et al. |
| 8,588,895 B2 | 11/2013 | Sanghera et al. |
| 8,588,896 B2 | 11/2013 | Allavatam |
| 8,594,775 B2 | 11/2013 | Ghosh et al. |
| 8,594,786 B2 | 11/2013 | Ousdigian |
| 8,600,489 B2 | 12/2013 | Warren et al. |
| 8,611,996 B2 | 12/2013 | Donofrio et al. |
| 8,626,280 B2 | 1/2014 | Allavatam et al. |
| 8,626,285 B2 | 1/2014 | Palreddy et al. |
| 8,700,152 B2 | 4/2014 | Palreddy et al. |
| 8,712,523 B2 | 4/2014 | Sanghera |
| 8,744,555 B2 | 6/2014 | Allavatam et al. |
| 8,750,989 B2 | 6/2014 | Bardy et al. |

(56) References Cited

U.S. PATENT DOCUMENTS

| | | | |
|---|---|---|---|
| 8,781,567 B2 | 7/2014 | Phillips et al. | |
| 8,781,602 B2 | 7/2014 | Sanghera et al. | |
| 8,788,023 B2 | 7/2014 | Sanghera et al. | |
| 8,825,157 B2 | 9/2014 | Warren et al. | |
| 8,983,586 B2 | 3/2015 | Zhang | |
| 2002/0058878 A1 | 5/2002 | Kohler et al. | |
| 2002/0165459 A1 | 11/2002 | Starobin et al. | |
| 2003/0083587 A1 | 5/2003 | Ferek-Petric | |
| 2003/0097153 A1 | 5/2003 | Bardy et al. | |
| 2003/0120312 A1 | 6/2003 | Cammilli et al. | |
| 2004/0015197 A1 | 1/2004 | Gunderson | |
| 2004/0021523 A1 | 2/2004 | Sadowy et al. | |
| 2004/0030256 A1 | 2/2004 | Lin | |
| 2004/0049120 A1 | 3/2004 | Cao et al. | |
| 2004/0059237 A1 | 3/2004 | Narayan et al. | |
| 2004/0088018 A1* | 5/2004 | Sawchuk et al. | 607/27 |
| 2004/0093037 A1 | 5/2004 | Henry | |
| 2004/0111121 A1 | 6/2004 | Brown et al. | |
| 2004/0220635 A1 | 11/2004 | Burnes | |
| 2004/0254613 A1 | 12/2004 | Ostroff et al. | |
| 2005/0038478 A1 | 2/2005 | Klepfer et al. | |
| 2006/0025822 A1 | 2/2006 | Zhang | |
| 2006/0042809 A1 | 3/2006 | Neufeld et al. | |
| 2006/0217621 A1 | 9/2006 | Kim et al. | |
| 2007/0232948 A1 | 10/2007 | Stadler et al. | |
| 2007/0233196 A1 | 10/2007 | Stadler et al. | |
| 2007/0233198 A1 | 10/2007 | Ghanem et al. | |
| 2007/0239220 A1 | 10/2007 | Greenhut et al. | |
| 2007/0270704 A1 | 11/2007 | Ghanem et al. | |
| 2007/0276445 A1 | 11/2007 | Sanghera et al. | |
| 2007/0276452 A1 | 11/2007 | Sanghera et al. | |
| 2008/0103535 A1 | 5/2008 | Ostroff et al. | |
| 2008/0132965 A1 | 6/2008 | Ostroff et al. | |
| 2008/0269813 A1* | 10/2008 | Greenhut et al. | 607/5 |
| 2008/0275516 A1 | 11/2008 | Ghanem et al. | |
| 2008/0275521 A1 | 11/2008 | Warren et al. | |
| 2008/0288009 A1 | 11/2008 | Kim et al. | |
| 2009/0005828 A1 | 1/2009 | Levine | |
| 2009/0054938 A1 | 2/2009 | Ostroff et al. | |
| 2010/0023083 A1 | 1/2010 | Eisinger et al. | |
| 2010/0114196 A1 | 5/2010 | Burnes et al. | |
| 2010/0331904 A1 | 12/2010 | Warren et al. | |
| 2011/0270102 A1 | 11/2011 | Zhang et al. | |
| 2011/0270103 A1 | 11/2011 | Zhang et al. | |
| 2011/0270107 A1 | 11/2011 | Zhang et al. | |
| 2011/0270110 A1 | 11/2011 | Zhang et al. | |
| 2011/0307024 A1 | 12/2011 | Ostroff et al. | |
| 2011/0319953 A1 | 12/2011 | Reed et al. | |
| 2012/0029335 A1 | 2/2012 | Sudam et al. | |
| 2012/0095520 A1 | 4/2012 | Zhang et al. | |
| 2012/0316612 A1 | 12/2012 | Warren et al. | |
| 2013/0030481 A1 | 1/2013 | Ghosh et al. | |
| 2013/0109985 A1 | 5/2013 | Gillberg et al. | |
| 2013/0150913 A1 | 6/2013 | Bornzin et al. | |
| 2013/0197381 A1 | 8/2013 | Charlton et al. | |
| 2013/0261471 A1 | 10/2013 | Saha et al. | |
| 2014/0275917 A1* | 9/2014 | Allavatam et al. | 600/374 |
| 2014/0296932 A1 | 10/2014 | Sanghera et al. | |
| 2015/0046396 A1 | 2/2015 | Limaye et al. | |
| 2015/0133954 A1 | 5/2015 | Seifert et al. | |

FOREIGN PATENT DOCUMENTS

| | | |
|---|---|---|
| EP | 1631350 | 3/2006 |
| EP | 1631352 | 3/2006 |
| EP | 1659934 | 5/2006 |
| EP | 1774906 | 4/2007 |
| EP | 1803485 | 7/2007 |
| EP | 1803486 | 7/2007 |
| EP | 1827220 | 9/2007 |
| EP | 1827598 | 9/2007 |
| EP | 2025363 | 2/2009 |
| EP | 2029224 | 3/2009 |
| EP | 2029225 | 3/2009 |
| EP | 2029226 | 3/2009 |
| EP | 2077889 | 7/2009 |
| EP | 2114244 | 11/2009 |
| EP | 2166938 A1 | 3/2010 |
| EP | 2268357 | 1/2011 |
| EP | 2268358 | 1/2011 |
| EP | 2313153 | 4/2011 |
| EP | 2446925 | 5/2012 |
| EP | 2446926 | 5/2012 |
| EP | 2455132 | 5/2012 |
| EP | 2459275 | 6/2012 |
| WO | WO 98/05254 A1 | 2/1998 |
| WO | 2004093974 A2 | 11/2004 |
| WO | WO 2004/105871 A1 | 12/2004 |
| WO | 200047278 | 10/2007 |
| WO | 2011136916 | 11/2011 |
| WO | 2012075119 A1 | 6/2012 |

OTHER PUBLICATIONS (PCT/US2015/023341) PCT Notification of Transmittal of the International Search Report and the Written Opinion of the International Searching Authority.

(PCT/US2015/023335) PCT Notification of Transmittal of the International Search Report and the Written Opinion of the International Searching Authority.

(PCT/US2015/025152) PCT Notification of Transmittal of the International Search Report and the Written Opinion of the International Searching Authority, dated Jun. 18, 2015, 9 pages.

(PCT/US2015/026277) PCT Notification of Transmittal of the International Search Report and the Written Opinion of the International Searching Authority, dated Jun. 26, 2015, 11 pages.

(PCT/US2015/026743) PCT Notification of Transmittal of the International Search Report and the Written Opinion of the International Searching Authority, dated Jul. 29, 2015, 10 pages.

(PCT/US2015/026745) PCT Notification of Transmittal of the International Search Report and the Written Opinion of the International Searching Authority, dated Aug. 6, 2015, 8 pages.

(PCT/US2015/026954) PCT Notification of Transmittal of the International Search Report and the Written Opinion of the International Searching Authority, dated Jul. 29, 2015, 11 pages.

(PCT/US2015/032809) PCT Notification of Transmittal of the International Search Report and the Written Opinion of the International Searching Authority, dated Aug. 6, 2015, 11 pages.

(PCT/US2015/025779) PCT Notification of Transmittal of the International Search Report and the Written Opinion of the International Searching Authority, dated Dec. 9, 2015, 8 pages.

* cited by examiner

METHOD AND APPARATUS FOR SELECTING A SENSING VECTOR CONFIGURATION IN A MEDICAL DEVICE

RELATED APPLICATION

The present application claims priority and other benefits from U.S. Provisional Patent Application Ser. No. 61/983,499, filed Apr. 24, 2014, entitled "METHOD AND APPARATUS FOR SELECTING A SENSING VECTOR CONFIGURATION IN A MEDICAL DEVICE", incorporated herein by reference in its entirety.

TECHNICAL FIELD

The disclosure relates generally to implantable medical devices and, in particular, to an apparatus and method for selecting a sensing vector in a medical device.

BACKGROUND

Implantable medical devices are available for preventing or treating cardiac arrhythmias by delivering anti-tachycardia pacing therapies and electrical shock therapies for cardioverting or defibrillating the heart. Such a device, commonly known as an implantable cardioverter defibrillator or "ICD", senses a patient's heart rhythm and classifies the rhythm according to a number of rate zones in order to detect episodes of tachycardia or fibrillation.

Upon detecting an abnormal rhythm, the ICD delivers an appropriate therapy. Pathologic forms of ventricular tachycardia can often be terminated by anti-tachycardia pacing therapies. Anti-tachycardia pacing therapies are followed by high-energy shock therapy when necessary. Termination of a tachycardia by a shock therapy is commonly referred to as "cardioversion." Ventricular fibrillation (VF) is a form of tachycardia that is a serious life-threatening condition and is normally treated by immediately delivering high-energy shock therapy. Termination of VF is commonly referred to as "defibrillation." Accurate arrhythmia detection and discrimination are important in selecting the appropriate therapy for effectively treating an arrhythmia and avoiding the delivery of unnecessary cardioversion/defibrillation (CV/DF) shocks, which are painful to the patient.

In past practice, ICD systems have employed intra-cardiac electrodes carried by transvenous leads for sensing cardiac electrical signals and delivering electrical therapies. Emerging ICD systems are adapted for subcutaneous or submuscular implantation and employ electrodes incorporated on the ICD housing and/or carried by subcutaneous or submuscular leads. These systems, referred to generally herein as "subcutaneous ICD" or "SubQ ICD" systems, do not rely on electrodes implanted in direct contact with the heart. SubQ ICD systems are less invasive and are therefore implanted more easily and quickly than ICD systems that employ intra-cardiac electrodes. However, greater challenges exist in reliably detecting cardiac arrhythmias using a subcutaneous system. The R-wave amplitude on a SubQ ECG signal may be on the order of one-tenth to one-one hundredth of the amplitude of intra-ventricular sensed R-waves. Furthermore, the signal quality of subcutaneously sensed ECG signals are likely to be more affected by myopotential noise, environmental noise, patient posture and patient activity than intra-cardiac myocardial electrogram (EGM) signals.

The ability of a subcutaneous ICD to detect tachyarrhythmias and reject noise depends on its ECG signal characteristics. ECG vectors with higher amplitude R-wave waves, higher frequency (high slew rate) R-waves, higher R/T wave ratios, lower frequency signal (e.g., P and T waves) around R-waves, lower susceptibility to skeletal myopotentials, and greater R-wave consistency from cycle to cycle are preferred to ECG vectors without these attributes. A subcutaneous ICD with a minimum of 2 ECG leads or vectors (using a minimum of 3 electrodes) in a plane may use these physical vectors to generate virtual ECG vectors using a linear combination of the physical vector ECGs. However, choosing the optimal vector may sometimes be a challenge given the changing environment of a subcutaneous system. As such, systems and methods that promote reliable and accurate sensing detection of arrhythmias using optimal available sensing vectors to sense ECG signals via subcutaneous electrodes are needed.

DETAILED DESCRIPTION

Figure 1:
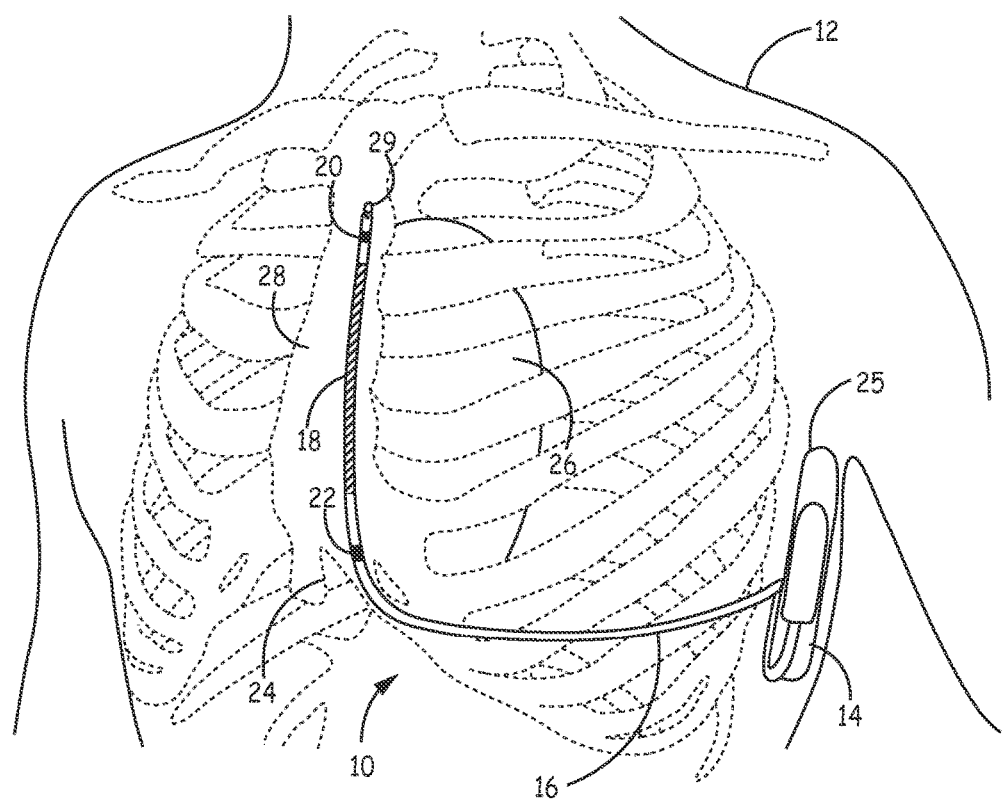
FIG. 1 is a conceptual diagram of a patient implanted with an example extravascular cardiac defibrillation system.

FIG. 1 is a conceptual diagram of a patient 12 implanted with an example extravascular cardiac defibrillation system 10. In the example illustrated in FIG. 1, extravascular cardiac defibrillation system 10 is an implanted subcutaneous ICD system. However, the techniques of this disclosure may also be utilized with other extravascular implanted cardiac defibrillation systems, such as a cardiac defibrillation system having a lead implanted at least partially in a substernal or submuscular location. Additionally, the techniques of this disclosure may also be utilized with other implantable systems, such as implantable pacing systems, implantable neurostimulation systems, drug delivery systems or other systems in which leads, catheters or other components are implanted at extravascular locations within patient 12. This disclosure, however, is described in the context of an implantable extravascular cardiac defibrillation system for purposes of illustration.

Extravascular cardiac defibrillation system 10 includes an implantable cardioverter defibrillator (ICD) 14 connected to at least one implantable cardiac defibrillation lead 16. ICD 14 of FIG. 1 is implanted subcutaneously on the left side of patient 12. Defibrillation lead 16, which is connected to ICD 14, extends medially from ICD 14 toward sternum 28 and xiphoid process 24 of patient 12. At a location near xiphoid process 24, defibrillation lead 16 bends or turns and extends subcutaneously superior, substantially parallel to sternum 28. In the example illustrated in FIG. 1, defibrillation lead 16 is implanted such that lead 16 is offset laterally to the left side of the body of sternum 28 (i.e., towards the left side of patient 12).

Defibrillation lead 16 is placed along sternum 28 such that a therapy vector between defibrillation electrode 18 and a second electrode (such as a housing or can 25 of ICD 14 or an electrode placed on a second lead) is substantially across the ventricle of heart 26. The therapy vector may, in one example, be viewed as a line that extends from a point on the defibrillation electrode 18 to a point on the housing or can 25 of ICD 14. In another example, defibrillation lead 16 may be placed along sternum 28 such that a therapy vector between defibrillation electrode 18 and the housing or can 25 of ICD 14 (or other electrode) is substantially across an atrium of heart 26. In this case, extravascular ICD system 10 may be used to provide atrial therapies, such as therapies to treat atrial fibrillation.

The embodiment illustrated in FIG. 1 is an example configuration of an extravascular ICD system 10 and should not be considered limiting of the techniques described herein. For example, although illustrated as being offset laterally from the midline of sternum 28 in the example of FIG. 1, defibrillation lead 16 may be implanted such that lead 16 is offset to the right of sternum 28 or more centrally located over sternum 28. Additionally, defibrillation lead 16 may be implanted such that it is not substantially parallel to sternum 28, but instead offset from sternum 28 at an angle (e.g., angled lateral from sternum 28 at either the proximal or distal end). As another example, the distal end of defibrillation lead 16 may be positioned near the second or third rib of patient 12. However, the distal end of defibrillation lead 16 may be positioned further superior or inferior depending on the location of ICD 14, location of electrodes 18, 20, and 22, or other factors.

Although ICD 14 is illustrated as being implanted near a midaxillary line of patient 12, ICD 14 may also be implanted at other subcutaneous locations on patient 12, such as further posterior on the torso toward the posterior axillary line, further anterior on the torso toward the anterior axillary line, in a pectoral region, or at other locations of patient 12. In instances in which ICD 14 is implanted pectorally, lead 16 would follow a different path, e.g., across the upper chest area and inferior along sternum 28. When the ICD 14 is implanted in the pectoral region, the extravascular ICD system may include a second lead including a defibrillation electrode that extends along the left side of the patient such that the defibrillation electrode of the second lead is located along the left side of the patient to function as an anode or cathode of the therapy vector of such an ICD system.

ICD 14 includes a housing or can 25 that forms a hermetic seal that protects components within ICD 14. The housing 25 of ICD 14 may be formed of a conductive material, such as titanium or other biocompatible conductive material or a combination of conductive and non-conductive materials. In some instances, the housing 25 of ICD 14 functions as an electrode (referred to as a housing electrode or can electrode) that is used in combination with one of electrodes 18, 20, or 22 to deliver a therapy to heart 26 or to sense electrical activity of heart 26. ICD 14 may also include a connector assembly (sometimes referred to as a connector block or header) that includes electrical feedthroughs through which electrical connections are made between conductors within defibrillation lead 16 and electronic components included within the housing. Housing may enclose one or more components, including processors, memories, transmitters, receivers, sensors, sensing circuitry, therapy circuitry and other appropriate components (often referred to herein as modules).

Defibrillation lead 16 includes a lead body having a proximal end that includes a connector configured to connect to ICD 14 and a distal end that includes one or more electrodes 18, 20, and 22. The lead body of defibrillation lead 16 may be formed from a non-conductive material, including silicone, polyurethane, fluoropolymers, mixtures thereof, and other appropriate materials, and shaped to form one or more lumens within which the one or more conductors extend. However, the techniques are not limited to such constructions. Although defibrillation lead 16 is illustrated as including three electrodes 18, 20 and 22, defibrillation lead 16 may include more or fewer electrodes.

Defibrillation lead 16 includes one or more elongated electrical conductors (not illustrated) that extend within the lead body from the connector on the proximal end of defibrillation lead 16 to electrodes 18, 20 and 22. In other words, each of the one or more elongated electrical conductors contained within the lead body of defibrillation lead 16 may engage with respective ones of electrodes 18, 20 and 22. When the connector at the proximal end of defibrillation lead 16 is connected to ICD 14, the respective conductors may electrically couple to circuitry, such as a therapy module or a sensing module, of ICD 14 via connections in connector assembly, including associated feedthroughs. The electrical conductors transmit therapy from a therapy module within ICD 14 to one or more of electrodes 18, 20 and 22 and transmit sensed electrical signals from one or more of electrodes 18, 20 and 22 to the sensing module within ICD 14.

ICD 14 may sense electrical activity of heart 26 via one or more sensing vectors that include combinations of electrodes 20 and 22 and the housing or can 25 of ICD 14. For example, ICD 14 may obtain electrical signals sensed using a sensing vector between electrodes 20 and 22, obtain electrical signals sensed using a sensing vector between electrode 20 and the conductive housing or can 25 of ICD 14, obtain electrical signals sensed using a sensing vector between electrode 22 and the conductive housing or can 25 of ICD 14, or a combination thereof. In some instances, ICD 14 may sense cardiac electrical signals using a sensing vector that includes defibrillation electrode 18, such as a sensing vector between defibrillation electrode 18 and one of electrodes 20 or 22, or a sensing vector between defibrillation electrode 18 and the housing or can 25 of ICD 14.

ICD may analyze the sensed electrical signals to detect tachycardia, such as ventricular tachycardia or ventricular fibrillation, and in response to detecting tachycardia may generate and deliver an electrical therapy to heart 26. For example, ICD 14 may deliver one or more defibrillation shocks via a therapy vector that includes defibrillation electrode 18 of defibrillation lead 16 and the housing or can 25. Defibrillation electrode 18 may, for example, be an elongated coil electrode or other type of electrode. In some instances, ICD 14 may deliver one or more pacing therapies prior to or after delivery of the defibrillation shock, such as anti-tachycardia pacing (ATP) or post shock pacing. In these instances, ICD 14 may generate and deliver pacing pulses via therapy vectors that include one or both of electrodes 20 and 22 and/or the housing or can 25. Electrodes 20 and 22 may comprise ring electrodes, hemispherical electrodes, coil electrodes, helix electrodes, segmented electrodes, directional electrodes, or other types of electrodes, or combination thereof. Electrodes 20 and 22 may be the same type of electrodes or different types of electrodes, although in the example of FIG. 1 both electrodes 20 and 22 are illustrated as ring electrodes.

Defibrillation lead 16 may also include an attachment feature 29 at or toward the distal end of lead 16. The attachment feature 29 may be a loop, link, or other attachment feature. For example, attachment feature 29 may be a loop formed by a suture. As another example, attachment feature 29 may be a loop, link, ring of metal, coated metal or a polymer. The attachment feature 29 may be formed into any of a number of shapes with uniform or varying thickness and varying dimensions. Attachment feature 29 may be integral to the lead or may be added by the user prior to implantation. Attachment feature 29 may be useful to aid in implantation of lead 16 and/or for securing lead 16 to a desired implant location. In some instances, defibrillation lead 16 may include a fixation mechanism in addition to or instead of the attachment feature. Although defibrillation lead 16 is illustrated with an attachment feature 29, in other examples lead 16 may not include an attachment feature 29.

Lead 16 may also include a connector at the proximal end of lead 16, such as a DF4 connector, bifurcated connector (e.g., DF-1/IS-1 connector), or other type of connector. The connector at the proximal end of lead 16 may include a terminal pin that couples to a port within the connector assembly of ICD 14. In some instances, lead 16 may include an attachment feature at the proximal end of lead 16 that may be coupled to an implant tool to aid in implantation of lead 16. The attachment feature at the proximal end of the lead may separate from the connector and may be either integral to the lead or added by the user prior to implantation.

Defibrillation lead 16 may also include a suture sleeve or other fixation mechanism (not shown) located proximal to electrode 22 that is configured to fixate lead 16 near the xiphoid process or lower sternum location. The fixation mechanism (e.g., suture sleeve or other mechanism) may be integral to the lead or may be added by the user prior to implantation.

The example illustrated in FIG. 1 is exemplary in nature and should not be considered limiting of the techniques described in this disclosure. For instance, extravascular cardiac defibrillation system 10 may include more than one lead. In one example, extravascular cardiac defibrillation system 10 may include a pacing lead in addition to defibrillation lead 16.

In the example illustrated in FIG. 1, defibrillation lead 16 is implanted subcutaneously, e.g., between the skin and the ribs or sternum. In other instances, defibrillation lead 16 (and/or the optional pacing lead) may be implanted at other extravascular locations. In one example, defibrillation lead 16 may be implanted at least partially in a substernal location. In such a configuration, at least a portion of defibrillation lead 16 may be placed under or below the sternum in the mediastinum and, more particularly, in the anterior mediastinum. The anterior mediastinum is bounded laterally by pleurae, posteriorly by pericardium, and anteriorly by sternum 28. Defibrillation lead 16 may be at least partially implanted in other extra-pericardial locations, i.e., locations in the region around, but not in direct contact with, the outer surface of heart 26. These other extra-pericardial locations may include in the mediastinum but offset from sternum 28, in the superior mediastinum, in the middle mediastinum, in the posterior mediastinum, in the sub-xiphoid or inferior xiphoid area, near the apex of the heart, or other location not in direct contact with heart 26 and not subcutaneous. In still further instances, the lead may be implanted at a pericardial or epicardial location outside of the heart 26.

Figure 2:
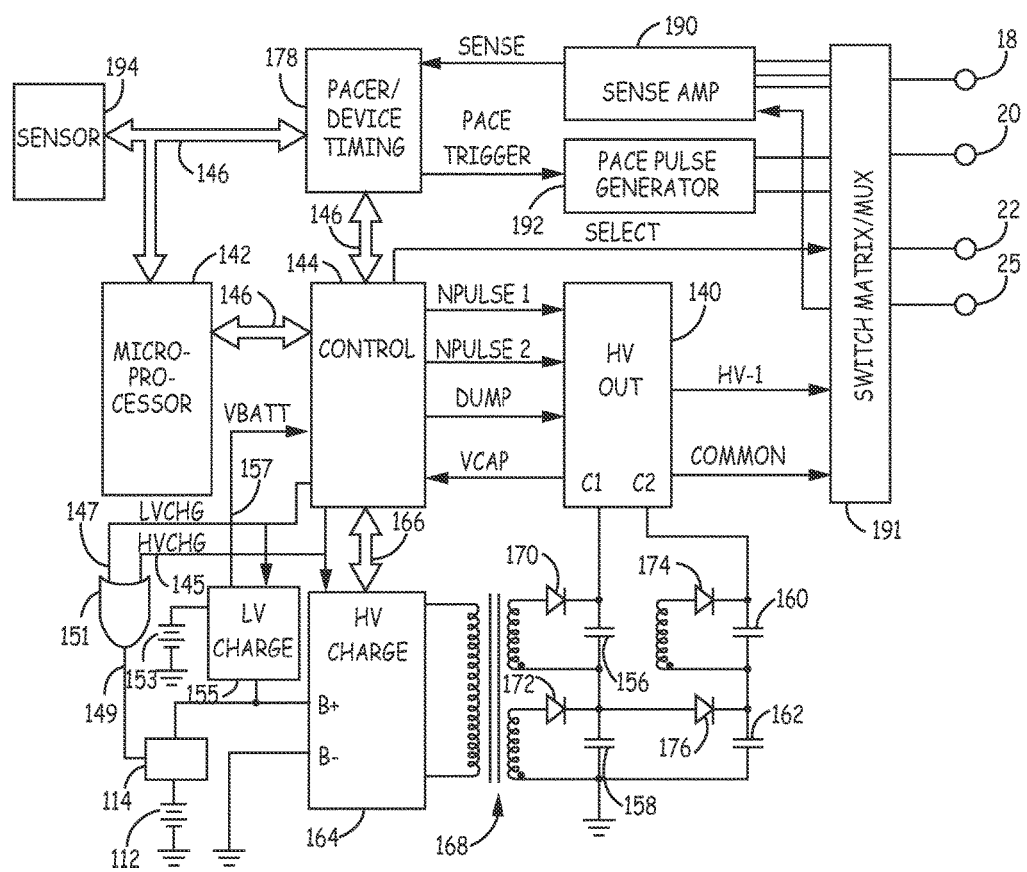
FIG. 2 is an exemplary schematic diagram of electronic circuitry within a hermetically sealed housing of a subcutaneous device according to an embodiment of the present invention.

FIG. 2 is an exemplary schematic diagram of electronic circuitry within a hermetically sealed housing of a subcutaneous device according to an embodiment of the present invention. As illustrated in FIG. 2, subcutaneous device 14 includes a low voltage battery 153 coupled to a power supply (not shown) that supplies power to the circuitry of the subcutaneous device 14 and the pacing output capacitors to supply pacing energy in a manner well known in the art. The low voltage battery 153 may be formed of one or two conventional $LiCF_x$, $LiMnO_2$ or $LiI_2$ cells, for example. The subcutaneous device 14 also includes a high voltage battery 112 that may be formed of one or two conventional LiSVO or $LiMnO_2$ cells. Although two both low voltage battery and a high voltage battery are shown in FIG. 2, according to an embodiment of the present invention, the device 14 could utilize a single battery for both high and low voltage uses.

Further referring to FIG. 2, subcutaneous device 14 functions are controlled by means of software, firmware and hardware that cooperatively monitor the ECG signal, determine when a cardioversion-defibrillation shock or pacing is necessary, and deliver prescribed cardioversion-defibrillation and pacing therapies. The subcutaneous device 14 may incorporate circuitry set forth in commonly assigned U.S. Pat. No. 5,163,427 "Apparatus for Delivering Single and Multiple Cardioversion and Defibrillation Pulses" to Keimel and U.S. Pat. No. 5,188,105 "Apparatus and Method for Treating a Tachyarrhythmia" to Keimel for selectively delivering single phase, simultaneous biphasic and sequential biphasic cardioversion-defibrillation shocks typically employing ICD IPG housing electrodes 28 coupled to the COMMON output 123 of high voltage output circuit 140 and cardioversion-defibrillation electrode 24 disposed posterially and subcutaneously and coupled to the HVI output 113 of the high voltage output circuit 140.

The cardioversion-defibrillation shock energy and capacitor charge voltages can be intermediate to those supplied by ICDs having at least one cardioversion-defibrillation electrode in contact with the heart and most AEDs having cardioversion-defibrillation electrodes in contact with the skin. The typical maximum voltage necessary for ICDs using most biphasic waveforms is approximately 750 Volts with an associated maximum energy of approximately 40 Joules. The typical maximum voltage necessary for AEDs is approximately 2000-5000 Volts with an associated maximum energy of approximately 200-360 Joules depending upon the model and waveform used. The subcutaneous device 14 of the present invention uses maximum voltages in the range of about 300 to approximately 1500 Volts and is associated with energies of approximately 25 to 150 joules or more. The total high voltage capacitance could range from about 50 to about 300 microfarads. Such cardioversion-defibrillation shocks are only delivered when a malignant tachyarrhythmia, e.g., ventricular fibrillation is detected through processing of the far field cardiac ECG employing the detection algorithms as described herein below.

In FIG. 2, sense amp 190 in conjunction with pacer/device timing circuit 178 processes the far field ECG sense signal that is developed across a particular ECG sense vector defined by a selected pair of the subcutaneous electrodes 18, 20, 22 and the can or housing 25 of the device 14, or, optionally, a virtual signal (i.e., a mathematical combination of two vectors) if selected. For example, the device may generate a virtual vector signal as described in U.S. Pat. No. 6,505,067 "System and Method for Deriving Virtual ECG or EGM Signal" to Lee, et al; both patents incorporated herein by reference in their entireties. In addition, vector selection may be selected by the patient's physician and programmed via a telemetry link from a programmer.

The selection of the sensing electrode pair is made through the switch matrix/MUX 191 in a manner to provide the most reliable sensing of the ECG signal of interest, which would be the R wave for patients who are believed to be at risk of ventricular fibrillation leading to sudden death. The far field ECG signals are passed through the switch matrix/MUX 191 to the input of the sense amplifier 190 that, in conjunction with pacer/device timing circuit 178, evaluates the sensed EGM. Bradycardia, or asystole, is typically determined by an escape interval timer within the pacer timing circuit 178 and/or the control circuit 144. Pace Trigger signals are applied to the pacing pulse generator 192 generating pacing stimulation when the interval between successive R-waves exceeds the escape interval. Bradycardia pacing is often temporarily provided to maintain cardiac output after delivery of a cardioversion-defibrillation shock that may cause the heart to slowly beat as it recovers back to normal function. Sensing subcutaneous far field signals in the presence of noise may be aided by the use of appropriate denial and extensible accommodation periods as described in U.S. Pat. No. 6,236,882 "Noise Rejection for Monitoring ECGs" to Lee, et al and incorporated herein by reference in its' entirety.

Detection of a malignant tachyarrhythmia is determined in the Control circuit 144 as a function of the intervals between R-wave sense event signals that are output from the pacer/device timing 178 and sense amplifier circuit 190 to the timing and control circuit 144. It should be noted that the present invention utilizes not only interval based signal analysis method but also supplemental sensors and morphology processing method and apparatus as described herein below.

Supplemental sensors such as tissue color, tissue oxygenation, respiration, patient activity and the like may be used to contribute to the decision to apply or withhold a defibrillation therapy as described generally in U.S. Pat. No. 5,464,434 "Medical Interventional Device Responsive to Sudden Hemodynamic Change" to Alt and incorporated herein by reference in its entirety. Sensor processing block 194 provides sensor data to microprocessor 142 via data bus 146. Specifically, patient activity and/or posture may be determined by the apparatus and method as described in U.S. Pat. No. 5,593,431 "Medical Service Employing Multiple DC Accelerometers for Patient Activity and Posture Sensing and Method" to Sheldon and incorporated herein by reference in its entirety. Patient respiration may be determined by the apparatus and method as described in U.S. Pat. No. 4,567,892 "Implantable Cardiac Pacemaker" to Plicchi, et al and incorporated herein by reference in its entirety. Patient tissue oxygenation or tissue color may be determined by the sensor apparatus and method as described in U.S. Pat. No. 5,176,137 to Erickson, et al and incorporated herein by reference in its entirety. The oxygen sensor of the '137 patent may be located in the subcutaneous device pocket or, alternatively, located on the lead 18 to enable the sensing of contacting or near-contacting tissue oxygenation or color.

Certain steps in the performance of the detection algorithm criteria are cooperatively performed in microcomputer 142, including microprocessor, RAM and ROM, associated circuitry, and stored detection criteria that may be programmed into RAM via a telemetry interface (not shown) conventional in the art. Data and commands are exchanged between microcomputer 142 and timing and control circuit 144, pacer timing/amplifier circuit 178, and high voltage output circuit 140 via a bi-directional data/control bus 146. The pacer timing/amplifier circuit 178 and the control circuit 144 are clocked at a slow clock rate. The microcomputer 142 is normally asleep, but is awakened and operated by a fast clock by interrupts developed by each R-wave sense event, on receipt of a downlink telemetry programming instruction or upon delivery of cardiac pacing pulses to perform any necessary mathematical calculations, to perform tachycardia and fibrillation detection procedures, and to update the time intervals monitored and controlled by the timers in pacer/device timing circuitry 178.

When a malignant tachycardia is detected, high voltage capacitors 156, 158, 160, and 162 are charged to a pre-programmed voltage level by a high-voltage charging circuit 164. It is generally considered inefficient to maintain a constant charge on the high voltage output capacitors 156, 158, 160, 162. Instead, charging is initiated when control circuit 144 issues a high voltage charge command HVCHG delivered on line 145 to high voltage charge circuit 164 and charging is controlled by means of bi-directional control/data bus 166 and a feedback signal VCAP from the HV output circuit 140. High voltage output capacitors 156, 158, 160 and 162 may be of film, aluminum electrolytic or wet tantalum construction.

The negative terminal of high voltage battery 112 is directly coupled to system ground. Switch circuit 114 is normally open so that the positive terminal of high voltage battery 112 is disconnected from the positive power input of the high voltage charge circuit 164. The high voltage charge command HVCHG is also conducted via conductor 149 to the control input of switch circuit 114, and switch circuit 114 closes in response to connect positive high voltage battery voltage EXT B+ to the positive power input of high voltage charge circuit 164. Switch circuit 114 may be, for example, a field effect transistor (FET) with its source-to-drain path interrupting the EXT B+ conductor 118 and its gate receiving the HVCHG signal on conductor 145. High voltage charge circuit 164 is thereby rendered ready to begin charging the high voltage output capacitors 156, 158, 160, and 162 with charging current from high voltage battery 112.

High voltage output capacitors 156, 158, 160, and 162 may be charged to very high voltages, e.g., 300-1500V, to be discharged through the body and heart between the electrode pair of subcutaneous cardioversion-defibrillation electrodes 113 and 123. The details of the voltage charging circuitry are also not deemed to be critical with regard to practicing the present invention; one high voltage charging circuit believed to be suitable for the purposes of the present invention is disclosed. High voltage capacitors 156, 158, 160 and 162 may be charged, for example, by high voltage charge circuit 164 and a high frequency, high-voltage transformer 168 as described in detail in commonly assigned U.S. Pat. No. 4,548,209 "Energy Converter for Implantable Cardioverter" to Wielders, et al. Proper charging polarities are maintained by diodes 170, 172, 174 and 176 interconnecting the output windings of high-voltage transformer 168 and the capacitors 156, 158, 160, and 162. As noted above, the state of capacitor charge is monitored by circuitry within the high voltage output circuit 140 that provides a VCAP, feedback signal indicative of the voltage to the timing and control circuit 144. Timing and control circuit 144 terminates the high voltage charge command HVCHG when the VCAP signal matches the programmed capacitor output voltage, i.e., the cardioversion-defibrillation peak shock voltage.

Control circuit 144 then develops first and second control signals NPULSE 1 and NPULSE 2, respectively, that are applied to the high voltage output circuit 140 for triggering the delivery of cardioverting or defibrillating shocks. In particular, the NPULSE 1 signal triggers discharge of the first capacitor bank, comprising capacitors 156 and 158. The NPULSE 2 signal triggers discharge of the first capacitor bank and a second capacitor bank, comprising capacitors 160 and 162. It is possible to select between a plurality of output pulse regimes simply by modifying the number and time order of assertion of the NPULSE 1 and NPULSE 2 signals. The NPULSE 1 signals and NPULSE 2 signals may be provided sequentially, simultaneously or individually. In this way, control circuitry 144 serves to control operation of the high voltage output stage 140, which delivers high energy cardioversion-defibrillation shocks between the pair of the cardioversion-defibrillation electrodes 18 and 25 coupled to the HV-1 and COMMON output as shown in FIG. 2.

Thus, subcutaneous device 14 monitors the patient's cardiac status and initiates the delivery of a cardioversion-defibrillation shock through the cardioversion-defibrillation electrodes 18 and 25 in response to detection of a tachyarrhythmia requiring cardioversion-defibrillation. The high HVCHG signal causes the high voltage battery 112 to be connected through the switch circuit 114 with the high voltage charge circuit 164 and the charging of output capacitors 156, 158, 160, and 162 to commence. Charging continues until the programmed charge voltage is reflected by the VCAP signal, at which point control and timing circuit 144 sets the HVCHG signal low terminating charging and opening switch circuit 114. The subcutaneous device 14 can be programmed to attempt to deliver cardioversion shocks to the heart in the manners described above in timed synchrony with a detected R-wave or can be programmed or fabricated to deliver defibrillation shocks to the heart in the manners described above without attempting to synchronize the delivery to a detected R-wave. Episode data related to the detection of the tachyarrhythmia and delivery of the cardioversion-defibrillation shock can be stored in RAM for uplink telemetry transmission to an external programmer as is well known in the art to facilitate in diagnosis of the patient's cardiac state. A patient receiving the device 14 on a prophylactic basis would be instructed to report each such episode to the attending physician for further evaluation of the patient's condition and assessment for the need for implantation of a more sophisticated ICD.

Subcutaneous device 14 desirably includes telemetry circuit (not shown in FIG. 2), so that it is capable of being programmed by means of external programmer 20 via a 2-way telemetry link (not shown). Uplink telemetry allows device status and diagnostic/event data to be sent to external programmer 20 for review by the patient's physician. Downlink telemetry allows the external programmer via physician control to allow the programming of device function and the optimization of the detection and therapy for a specific patient. Programmers and telemetry systems suitable for use in the practice of the present invention have been well known for many years. Known programmers typically communicate with an implanted device via a bi-directional radio-frequency telemetry link, so that the programmer can transmit control commands and operational parameter values to be received by the implanted device, so that the implanted device can communicate diagnostic and operational data to the programmer. Programmers believed to be suitable for the purposes of practicing the present invention include the Models 9790 and CareLink® programmers, commercially available from Medtronic, Inc., Minneapolis, Minn.

Various telemetry systems for providing the necessary communications channels between an external programming unit and an implanted device have been developed and are well known in the art. Telemetry systems believed to be suitable for the purposes of practicing the present invention are disclosed, for example, in the following U.S. patents: U.S. Pat. No. 5,127,404 to Wyborny et al. entitled "Telemetry Format for Implanted Medical Device"; U.S. Pat. No. 4,374,382 to Markowitz entitled "Marker Channel Telemetry System for a Medical Device"; and U.S. Pat. No. 4,556,063 to Thompson et al. entitled "Telemetry System for a Medical Device". The Wyborny et al. '404, Markowitz '382, and Thompson et al. '063 patents are commonly assigned to the assignee of the present invention, and are each hereby incorporated by reference herein in their respective entireties.

According to an embodiment of the present invention, in order to automatically select the preferred ECG vector set, it is necessary to have an index of merit upon which to rate the quality of the signal. "Quality" is defined as the signal's ability to provide accurate heart rate estimation and accurate morphological waveform separation between the patient's usual sinus rhythm and the patient's ventricular tachyarrhythmia.

Appropriate indices may include R-wave amplitude, R-wave peak amplitude to waveform amplitude between R-waves (i.e., signal to noise ratio), low slope content, relative high versus low frequency power, mean frequency estimation, probability density function, or some combination of these metrics.

Automatic vector selection might be done at implantation or periodically (daily, weekly, monthly) or both. At implant, automatic vector selection may be initiated as part of an automatic device turn-on procedure that performs such activities as measure lead impedances and battery voltages. The device turn-on procedure may be initiated by the implanting physician (e.g., by pressing a programmer button) or, alternatively, may be initiated automatically upon automatic detection of device/lead implantation. The turn-on procedure may also use the automatic vector selection criteria to determine if ECG vector quality is adequate for the current patient and for the device and lead position, prior to suturing the subcutaneous device 14 device in place and closing the incision. Such an ECG quality indicator would allow the implanting physician to maneuver the device to a new location or orientation to improve the quality of the ECG signals as required. The preferred ECG vector or vectors may also be selected at implant as part of the device turn-on procedure. The preferred vectors might be those vectors with the indices that maximize rate estimation and detection accuracy. There may also be an a priori set of vectors that are preferred by the physician, and as long as those vectors exceed some minimum threshold, or are only slightly worse than some other more desirable vectors, the a priori preferred vectors are chosen. Certain vectors may be considered nearly identical such that they are not tested unless the a priori selected vector index falls below some predetermined threshold.

Depending upon metric power consumption and power requirements of the device, the ECG signal quality metric may be measured on the range of vectors (or alternatively, a subset) as often as desired. Data may be gathered, for example, on a minute, hourly, daily, weekly or monthly basis. More frequent measurements (e.g., every minute) may be averaged over time and used to select vectors based upon susceptibility of vectors to occasional noise, motion noise, or EMI, for example.

Alternatively, the subcutaneous device 14 may have an indicator/sensor of patient activity (piezo-resistive, accelerometer, impedance, or the like) and delay automatic vector measurement during periods of moderate or high patient activity to periods of minimal to no activity. One representative scenario may include testing/evaluating ECG vectors once daily or weekly while the patient has been determined to be asleep (using an internal clock (e.g., 2:00 am) or, alternatively, infer sleep by determining the patient's position (via a 2- or 3-axis accelerometer) and a lack of activity). In another possible scenario, the testing/evaluating ECG vectors may be performed once daily or weekly while the patient is known to be exercising.

If infrequent automatic, periodic measurements are made, it may also be desirable to measure noise (e.g., muscle, motion, EMI, etc.) in the signal and postpone the vector selection measurement until a period of time when the noise has subsided.

Subcutaneous device 14 may optionally have an indicator of the patient's posture (via a 2- or 3-axis accelerometer). This sensor may be used to ensure that the differences in ECG quality are not simply a result of changing posture/position. The sensor may be used to gather data in a number of postures so that ECG quality may be averaged over these postures, or otherwise combined, or, alternatively, selected for a preferred posture.

In one embodiment, vector quality metric calculations may be performed by the clinician using a programmer either at the time of implant, during a subsequent visit in a clinic setting, or remotely via a remote link with the device and the programmer. According to another embodiment, the vector quality metric calculations may be performed automatically for each available sensing vector by the device a predetermined number of times, such multiple times daily, once per day, weekly or on a monthly basis. In addition, the values could be averaged for each vector over the course of one week, for example. Averaging may consist of a moving average or recursive average depending on time weighting and memory considerations.

Figure 3:
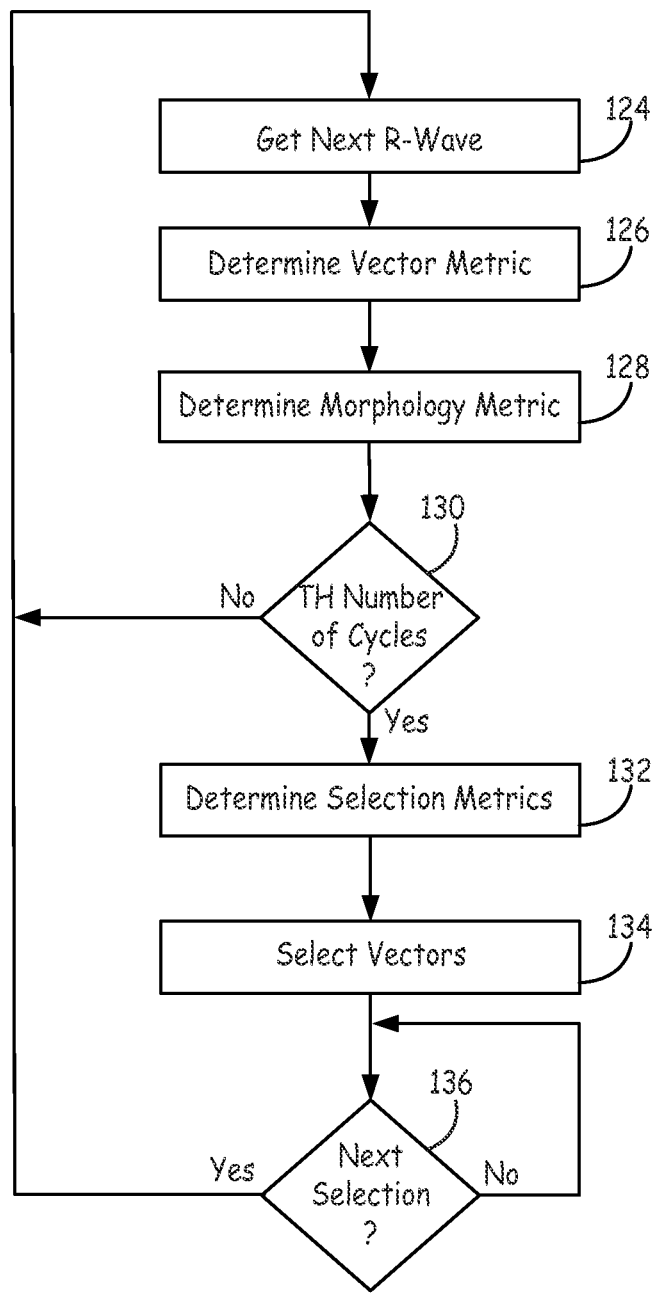
FIG. 3 is a flowchart of a method for selecting a sensing vector in a medical device, according to one embodiment.

FIG. 3 is a flowchart of a method for selecting a sensing vector in a medical device, according to one embodiment. As illustrated in FIG. 3, according to an embodiment of the disclosure, the device senses a cardiac signal for each available sensing vector 102-106, using sensing techniques known in the art, such as described, for example, in U.S. patent application Ser. No. 14/250,040 (U.S. Patent Publication No. 2015/0290468), incorporated herein by reference in it's entirety. The device obtains a sensed R-wave of the cardiac signal for each available sensing vector 102-106, Block 124, and determines both a vector quality metric, Block 126, for determining the quality of a sensing for the vector, and a morphology quality metric, Block 128, for determining the quality of a morphology analysis, associated with the sensed R-wave for that sensing vector 102-106, as described below. Once both a vector quality metric, Block 126 and a morphology metric, Block 128, associated with the sensed R-wave has been determined for each sensing vector 102-106, the device determines whether the vector quality metric and the morphology metric has been determined for a predetermined threshold number of cardiac cycles for each of the sensing vectors 102-106, Block 130. If the vector quality metric and the morphology metric has not been determined for the predetermined threshold number of cardiac cycles for each sensing vector 102-106, No in Block 130, the device gets the next R-wave 124 for each sensing vector 102-106, and the process is repeated for a next sensed cardiac cycle for each of the sensing vectors 102-106. According to one embodiment, the vector quality metric and the morphology metric is determined for 15 cardiac cycles, for example.

Once the vector metric and the morphology metric have been determined for the predetermined threshold number of cardiac cycles for each sensing vector 102-106, Yes in Block 130, the device determines selection metrics using the determined vector quality metrics and morphology metrics, Block 132, and selects one or more vectors, Block 134, to be utilized during subsequent sensing and arrhythmia detection by the device based on the determined selection metrics, as described below. Depending on the amount of time programmed to occur between updating of the sensing vectors 102-106, i.e., an hour, day, week or month, for example, the device waits until the next scheduled vector selection determination, Block 136, at which time the vector selection process is repeated.

Figure 4:
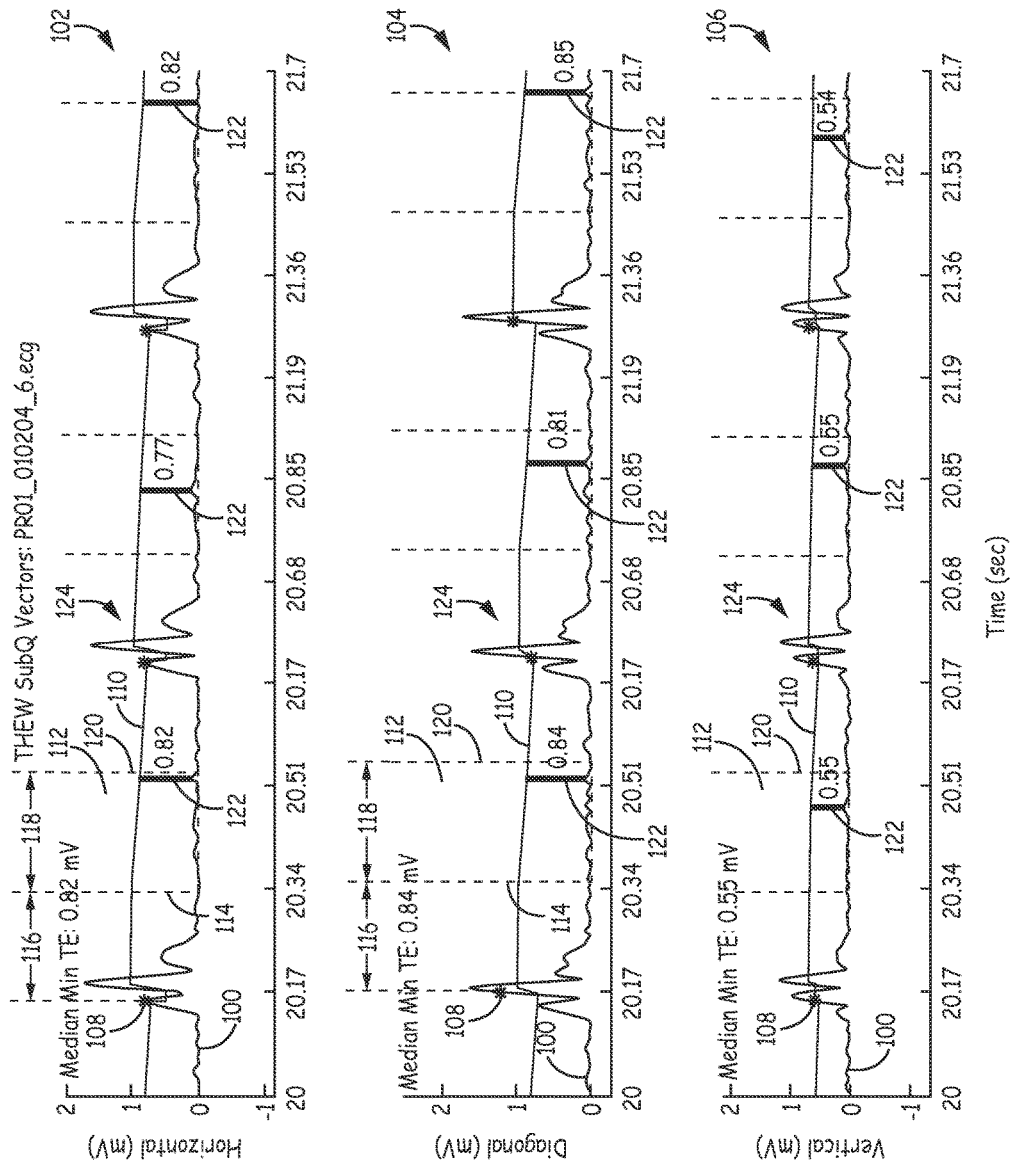
FIG. 4 is a graphical representation of cardiac signals sensed along multiple sensing vectors during selection of a sensing vector in a medical device according to one embodiment.

FIG. 4 is a graphical representation of cardiac signals sensed along multiple sensing vectors during selection of a sensing vector in a medical device according to one embodiment. As illustrated in FIG. 4, during the vector selection process, the device senses a cardiac signal 100 for each available sensing vector 102-106, using sensing techniques known in the art, such as described, for example, in U.S. patent application Ser. No. 14/250,040 (U.S. Patent Publication No. 2015/0290468), incorporated herein by reference in it's entirety. For example, as illustrated in FIG. 4, according to one embodiment, the device senses an ECG signal 100 from each of the available sensing vectors, including a horizontal sensing vector 102 extending between the housing or can 25 and electrode 22, a diagonal sensing vector 104 extending between the housing or can 25 and electrode 20, and a vertical sensing vector 106 extending between electrodes 20 and 22. The device determines a sensed R-wave 108 for each sensing vector 102-106 as occurring when the sensed signal exceeds a time-dependent self-adjusting sensing threshold 110.

Once the R-wave 108 is sensed, the device determines a vector quality metric and a morphology metric for the sensed R-wave, Blocks 126 and 128 of FIG. 3. As illustrated in FIG. 4, in order to determine the vector quality metric, Block 126 of FIG. 3, for example, the device sets a vector quality metric detection window 112, based on the sensed R-wave 108 for each of the sensing vectors 102-106, for determining a vector quality metric associated with the sensing vectors 102-106. According to an embodiment, the device sets a quality metric detection window 112 to start at a start point 114 located a predetermined distance 116 from the R-wave 108, and having a detection window width 118 so as to allow an analysis of the signal 100 to be performed in an expected range of the signal 100 where a T-wave of the QRS signal associated with the sensed R-wave 108 is likely to occur. For example, the device sets the quality metric detection window 112 as having a width 118 of approximately 200 ms, with a start point 114 of the quality metric detection window 112 located between approximately 150-180 milliseconds from the sensed R-wave 108, and the width 118 extending 200 ms from the detection window start point 114 to a detection window end point 120, i.e., at a distance of approximately 350-380 ms from the detected R-wave 108. Once the quality metric detection window 112 is set, the device determines a minimum signal difference 122 between the sensed signal 100 and the sensing threshold 110 within the quality metric detection window 112, i.e., the minimum distance extending between the sensed signal 100 and the sensing threshold 110. This determined minimum signal difference 122 for each of the three sensing vectors 102-106 is then set as the vector quality metric for the simultaneously sensed R-waves 108 in the sensing vectors, Block 126.

Figure 5:
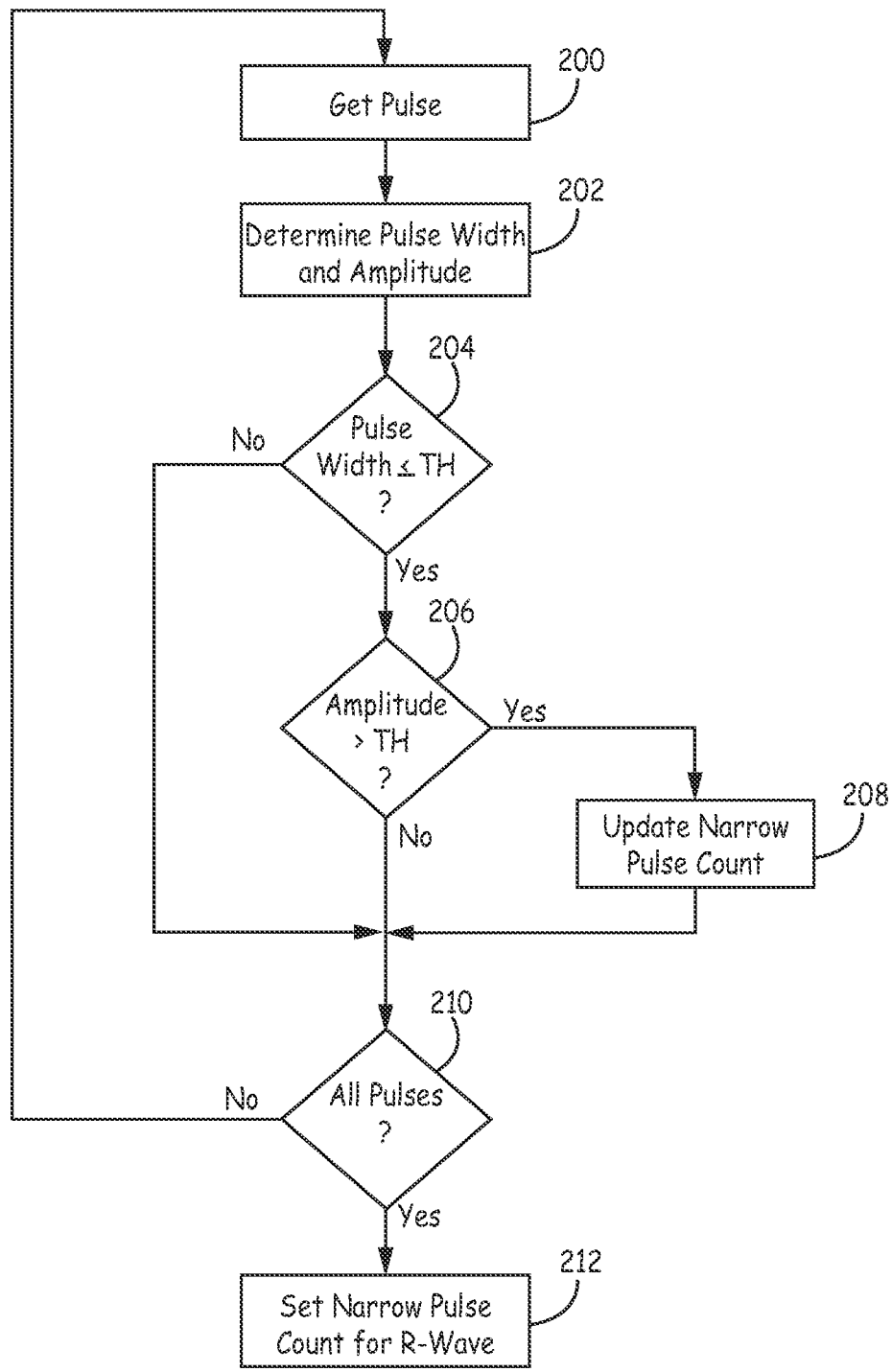
FIG. 5 is a flowchart of a method for determining a morphology metric for selecting a sensing vector, according to one embodiment.

FIG. 5 is a flowchart of a method for determining a morphology metric for selecting a sensing vector, according to one embodiment. In order to determine the morphology metric, Block 126 of FIG. 3, the device determines a narrow pulse count, i.e., pulse number, for the R-wave 108. For example, in order to determine the narrow pulse count for each R-wave 108 associated with the sensing vectors 102-106, the device determines individual pulses associated with the R-wave using known techniques, such as described in commonly assigned U.S. patent application Ser. No. 13/826,097 (U.S. Pat. No. 8,983,586) and Ser. No. 14/255,158 (U.S. Patent Publication No. US 2015/0297907), for example, incorporated herein by reference in their entireties. For each identified pulse, the device determines whether the width of the pulse is less than a predetermined threshold. In particular, as illustrated in FIG. 5, the device gets a single pulse of the identified pulses associated with the R-wave, Block 200, determines a pulse width associated with the pulse, Block 202, and determines whether the pulse width is less than or equal to a pulse width threshold, Block 204.

In addition to determining whether the pulse width of the individual pulse is less than or equal to the pulse width threshold, Yes in Block 204, the device may also determine whether the absolute amplitude of the pulse is greater than an amplitude threshold, Block 206. According to an embodiment, the pulse width threshold may be set as 23 milliseconds, for example, and the amplitude threshold is set as a fraction, such as one eighth, for example, of a maximum slope used in the determination of whether the slope threshold was met during the aligning of the beat with the template, described in commonly assigned U.S. patent application Ser. No. 13/826,097 (U.S. Pat. No. 8,983,586) and Ser. No. 14/255,158 (U.S. Patent Publication No. US 2015/0297907), incorporated herein by reference in their entireties.

While the pulse width determination, Block 204, is illustrated as occurring prior to the amplitude threshold determination, Block 206, it is understood that the determinations of Blocks 204 and 206 may be performed in any order. Therefore, if either the pulse width of the individual pulse is not less than or equal to the pulse width threshold, No in Block 204, or the absolute amplitude of the pulse is not greater than the amplitude threshold, No in Block 206, the pulse is determined not to be included in the narrow pulse count. The device continues by determining whether the determination of whether the number of pulses satisfying the narrow pulse count parameters has been made for all of the identified pulses for the R-wave beat, Block 210. If the determination has not been made for all of the identified pulses, No in Block 210, the device identifies the next pulse associated with the R-wave, Block 200, and the process of determining a narrow pulse count for that beat, Blocks 202-208, is repeated for the next pulse.

If both the pulse width of the individual pulse is less than or equal to the pulse width threshold, Yes in Block 204, and the absolute amplitude of the pulse is greater than the amplitude threshold, Yes in Block 206, the number of pulses satisfying the width and amplitude thresholds for the individual R-wave, i.e., the narrow pulse count, is increased by one, Block 208.

Once the determination has been made for all of the identified pulses associated with the R-wave, Yes in Block 210, the device sets the narrow pulse count for the R-wave, Block 212, equal to the resulting updated narrow pulse count, Block 208. In this way, the narrow pulse count for the R-wave is the total number of pulses of the identified pulses for the R-wave that satisfy both the width threshold, i.e., the number of pulses that have a pulse width less than 23 milliseconds, and the amplitude threshold, i.e., the number of pulses that have an absolute amplitude greater than one eighth of the maximum slope used during the aligning of the beat with the template, for example. The final narrow pulse count from Block 212 is then stored as the morphology metric for each R-wave.

In this way, after the process is repeated for multiple R-waves sensed along each of the sensing vectors 102-106 so that both the vector quality metric and the morphology metric has been determined for the predetermined threshold number of cardiac cycles for each of the sensing vectors 102-106, such as 15, for example, Block 130, the device determines the selection metrics, Block 132 of FIG. 3, i.e., a vector selection metric and a morphology selection metric. As illustrated in FIGS. 3 and 4, once the minimum signal difference 122 has been determined for all of the predetermined threshold number of cardiac cycles, Yes in Block 130, the device determines a vector selection metric for each vector 102-106 based on the 15 minimum signal differences 122 determined for that sensing vector. For example, according to an embodiment, the device determines the median of the 15 minimum signal differences 122 for each sensing vector and sets the vector selection metric for that sensing vector equal to the determined median of the associated minimum signal differences 122. Once a single vector selection metric is determined for each of the sensing vectors 102-106, the device ranks the vector selection metrics for the sensing vectors 102-106. For example, the device ranks the determined vector selection metrics from highest to lowest, so that in the example of FIG. 4, the diagonal sensing vector 104 would be ranked first since the median minimum signal difference for that vector was 0.84 millivolts, the horizontal sensing vector 102 would be ranked second, since the median minimum signal difference for that vector is 0.82 millivolts, and the vertical sensing vector 106 would be ranked last, since the median minimum signal difference for that sensing vector is 0.55 millivolts.

Similarly, in order to determine morphology selection metrics in Block 132 of FIG. 3, the device may determine an average, a mean or a maximum pulse count of the 15 determined narrow pulse counts for each of the sensing vectors 102-106. Based on the determined average, median or maximum narrow pulse count for R-waves simultaneously sensed along the sensing vectors 102-106, the device ranks the vectors based on the determined morphology selection metrics as being one of a low pulse count, a medium pulse count and a high pulse count. For example, according to one embodiment, if the average, mean or maximum pulse count associated with a sensing vector is greater than 5, the final pulse count for that vector, i.e., morphology selection metric, is determined to be "high". If the average, mean or maximum pulse count associated with a sensing vector is less than or equal to 5, but greater than or equal to 2, the final pulse count for that vector, i.e., morphology selection metric, is determined to be "medium". Otherwise, if the average, mean or maximum pulse count associated with a sensing vector is less than or equal to 1, the final pulse count for that vector, I.e., morphology selection metric, is determined to be "low".

Figure 6:
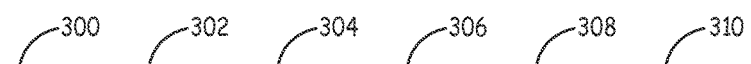
FIG. 6 is a chart illustrating a method of utilizing determined selection metrics for selecting a sensing vector, according to an exemplary embodiment.

According to another embodiment, the sensing vectors 102-106 may be relatively ranked based on the morphology selection metric, so that the sensing vector having the greatest pulse count would be identified as being "high", the sensing vector having the second greatest pulse count would be identified as being "medium", and the sensing vector having the lowest pulse count would be identified as being "low", FIG. 6 is a chart illustrating a method of utilizing determined selection metrics for selecting a sensing vector, according to an exemplary embodiment. As illustrated in FIG. 6, assuming that the result of the determination of the vector selection metric, described above, is that sensing vector 102 is ranked first, sensing vector 104 is ranked second and sensing vector 106 is ranked third, and if the sensing vectors 102-106 are relatively ranked based on the morphology selection metric, the six possible scenarios are shown, so that the result of the morphology selection metric may be illustrated by any one of six possible scenarios. In a first morphology selection scenario, 300, sensing vector 102 is determined to have a low relative narrow pulse count (i.e., relative to sensing vectors 104 and 106) over the 15 cardiac cycles, sensing vector 104 is determined to have a medium relative narrow pulse count (i.e., relative to sensing vectors 102 and 106), and sensing vector 106 is determined to have a high relative narrow pulse count (i.e., relative to sensing vectors 102 and 104). In a second morphology selection scenario, 302, sensing vector 102 is determined to have a low relative narrow pulse count over the 15 cardiac cycles, sensing vector 104 is determined to have a high relative narrow pulse count, and sensing vector 106 is determined to have a medium relative narrow pulse count.

In a third morphology selection scenario, 304, sensing vector 102 is determined to have a medium relative narrow pulse count over the 15 cardiac cycles, sensing vector 104 is determined to have a high relative narrow pulse count, and sensing vector 106 is determined to have a low relative narrow pulse count. In a fourth morphology selection scenario, 306, sensing vector 102 is determined to have a medium relative narrow pulse count over the 15 cardiac cycles, sensing vector 104 is determined to have a low relative narrow pulse count, and sensing vector 106 is determined to have a high relative narrow pulse count. In a fifth morphology selection scenario, 308, sensing vector 102 is determined to have a high relative narrow pulse count over the 15 cardiac cycles, sensing vector 104 is determined to have a low relative narrow pulse count, and sensing vector 106 is determined to have a medium relative narrow pulse count. Finally, in a sixth morphology selection scenario 310, sensing vector 102 is determined to have a high relative pulse count over the 15 cardiac cycles, sensing vector 104 is determined to have a medium relative narrow pulse count, and sensing vector 106 is determined to have a low relative narrow pulse count.

Figure 7:
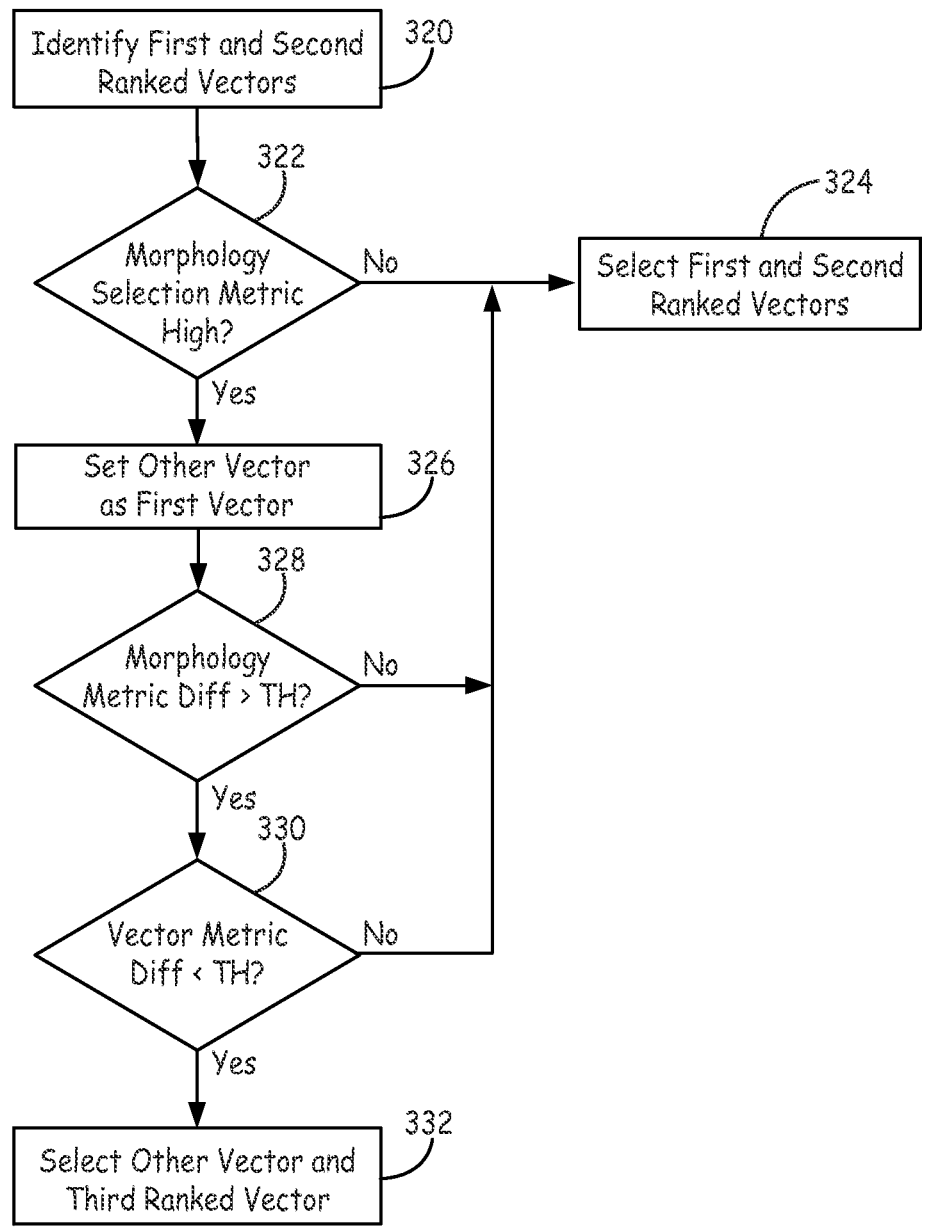
FIG. 7 is a flowchart of a method for selecting sensing vectors using determined vector selection metrics and morphology selection metrics according to an embodiment.

FIG. 7 is a flowchart of a method for selecting sensing vectors using determined vector selection metrics and morphology selection metrics according to an embodiment. As illustrated in FIGS. 6 and 7, once the vector selection metrics and the morphology selection metrics have been determined for the sensing vectors 102-106, the device identifies the resulting first and second ranked vectors, Block 320, which in the example of FIG. 6 are sensing vectors 102 and 104, and determines whether the morphology selection metric of one of the corresponding determined morphology selection metrics has a "High" pulse count, Block 322. In the example of FIG. 6, this occurs, Yes in Block 322, in morphology selection scenarios 302, 304, 308 and 310, and does not occur, No in Block 322, in morphology selection scenarios 300 and 306. If neither one of the determined morphology selection metrics associated with the first and second ranked vectors is a "High" morphology selection metric, No in Block 322, the first and second ranked vectors are selected as the sensing vectors, Block 324.

If the morphology selection metric of either the first ranked vector or the second ranked vector is a "High" morphology selection metric, Yes in Block 322, the device sets the other vector as the first ranked vector, Block 326. For example, in morphology selection metric scenarios 308 and 310, the second ranked vector, i.e.; sensing vector 104, is set as the first ranked vector and sensing vector 102 is set as the updated second ranked vector, and in morphology selection metric scenarios 302 and 304, the first ranked sensing vector, i.e., sensing vector 102 is set (remains) as the first ranked vector.

In order to determine which one of the remaining two sensing vectors is chosen as the second ranked vector, the device then determines whether a difference between the morphology metrics of the updated second and third vectors is less than a morphology metric difference threshold, Block 328 and whether a difference between the vector metrics of the updated second and third vectors is greater than a vector metric difference threshold, Block 330. For example, according to one embodiment, the device may determine in Block 328 whether the difference between the narrow pulse count determined, as described above, for the vector identified as having the "HIGH" morphology selection metric and the third ranked vector is greater than or equal to three.

By way of illustration, in morphology selection metric scenarios 308 and 310, the device determines whether the difference between sensing vector 102 and sensing vector 106 is greater than the morphology metric difference threshold by subtracting the morphology metric, i.e., narrow pulse count, determined above, for the third ranked sensing vector from the morphology metric determined for the vector identified as having the "HIGH" morphology selection metric, i.e., sensing vector 102. Similarly, in morphology selection metric scenarios 302 and 304, the device determines whether the difference between sensing vector 104 and sensing vector 106 is greater than the morphology metric difference threshold by subtracting the morphology metric, i.e., narrow pulse count, determined above, for the third ranked sensing vector from the morphology metric determined for the vector identified as having the "HIGH" morphology selection metric, i.e., sensing vector 104.

If the difference between the morphology metrics of the updated second and third vectors is not greater than a morphology metric difference threshold, No in Block 328, the first and second ranked vectors are selected as the sensing vectors, Block 324.

Similarly, for example, according to one embodiment, in order to determine whether a difference between the vector metrics of the updated second and third vectors is less than a vector metric difference threshold, Block 330, the device may determine whether the difference between the minimum signal difference determined, as described above, for the vector identified as having the "HIGH" morphology selection metric and the third ranked vector is less than a nominal minimum threshold, such as 0.10 millivolts, for example.

By way of illustration, in morphology selection metric scenarios 308 and 310, the device determines whether the difference between sensing vector 102 and sensing vector 106 is greater than the vector metric difference threshold by subtracting the vector metric, i.e., minimum signal difference, determined above, for the third ranked sensing vector from the vector metric determined for the vector identified as having the "HIGH" morphology selection metric, i.e., sensing vector 102. Similarly, in morphology selection metric scenarios 302 and 304, the device determines whether the difference between sensing vector 104 and sensing vector 106 is less than the vector metric difference threshold by subtracting the vector metric, i.e., minimum signal difference, determined above, for the third ranked sensing vector from the vector metric determined for the vector identified as having the "HIGH" morphology selection metric, i.e., sensing vector 104.

If the difference between the vector metrics of the updated second and third vectors is not less than the vector metric difference threshold, No in Block 330, the first and second ranked vectors are selected as the sensing vectors, Block 324. If both the difference between the morphology metrics of the updated second and third vectors is greater than the morphology metric difference threshold, Yes in Block 328, and the difference between the vector metrics of the updated second and third vectors is less than the vector metric difference threshold, Yes in Block 330, the updated first and the third vectors are selected as the sensing vectors, Block 332. For example, assuming both the morphology metric difference threshold and the vector metric difference threshold are satisfied, Yes in Blocks 328 and 330, in morphology selection metric scenarios 308 and 310, vectors 104 and 106 are selected as the sensing vectors, and in morphology selection metric scenarios 302 and 304, vectors 102 and 106 are selected as sensing vectors.

In some instances, the morphology selection metric for two or more of the sensing vectors 102-106 may have the same ranking. Therefore, according to one embodiment, if two sensing vectors have the same morphology selection metric, the device may select the first and second ranked vectors from the vector selection metric, i.e., vectors 102 and 104 in the example shown in FIG. 7, as the sensing vectors to be utilized. Or according to another embodiment, if the morphology selection metric for two or more of the sensing vectors 102-106 is "High", then the device may select the first and second ranked vectors from the vector selection metric, i.e., vectors 102 and 104 in the example shown in FIG. 7, as the sensing vectors to be utilized. In both situations, the sensing vectors 102 and 104 were chosen based only on the determined minimum signal differences for the sensing vectors 102-106, and therefore no updating of the first and second raked sensing vectors would occur.

It is understood that in addition to the three sensing vectors 102-106 described above, optionally, a virtual signal (i.e., a mathematical combination of two vectors) may also be utilized in addition to, thus utilizing more than three sensing vectors, or in place of the sensing vectors described. For example, the device may generate a virtual vector signal as described in U.S. Pat. No. 6,505,067 "System and Method for Deriving Virtual ECG or EGM Signal" to Lee, et al; both patents incorporated herein by reference in their entireties. In addition, vector selection may be selected by the patient's physician and programmed via a telemetry link from a programmer.

In addition, while the use of a minimum signal difference is described, the device may utilize other selection criteria for ranking vectors. For example, according one embodiment, the device may determine, for each vector, a maximum signal amplitude within the detection window for each R-wave, determine the difference between the maximum amplitude and the sensing threshold for each of the maximum amplitudes, and determine a median maximum amplitude difference for each sensing vector over 15 cardiac cycles. The device would then select the vector(s) having the greatest median maximum amplitude difference as the sensing vector(s) to be utilized during subsequent sensing and arrhythmia detection by the device.

Thus, a method and apparatus for selecting a sensing vector configuration in a medical device have been presented in the foregoing description with reference to specific embodiments. It is appreciated that various modifications to the referenced embodiments may be made without departing from the scope of the disclosure as set forth in the following claims.

I claim:

1. A method of determining sensing vectors in a medical device, comprising:
    sensing cardiac signals on a plurality of sensing vectors formed from a plurality of electrodes;
    determining, for each of the plurality of sensing vectors, a sensing vector metric of the sensed cardiac signals;
    determining, for each of the plurality of sensing vectors, a morphology metric associated with a morphology of the sensed cardiac signals, wherein determining the morphology metric comprises:
        sensing an R-wave in response to the cardiac signal exceeding a sensing threshold;
        determining pulses associated with the sensed R-wave;
        determining, for each pulse, whether a pulse width of the pulse is less than a pulse width threshold;
        determining, for each pulse, whether a pulse amplitude of the pulse is greater than a pulse amplitude threshold;
        determining a number of the determined pulses having both a pulse width less than the pulse width threshold and a pulse amplitude greater than the pulse amplitude threshold; and
        setting the morphology metric equal to the determined number of pulses;
    determining, for each of the plurality of sensing vectors, vector selection metrics based on at least the determined sensing vector metric and the determined morphology metric; and
    selecting a sensing vector of the plurality of sensing vectors based on at least the determined selection metrics.

2. The method of claim 1, wherein determining a sensing vector metric comprises:
    setting a window of time determined based on the sensed R-wave
    determining signal differences between the sensed cardiac signal and the sensing threshold during the window of time; and
    setting the sensing vector metric based on at least the determined signal differences.

3. The method of claim 2, wherein selecting a sensing vector comprises:
    selecting a sensing vector of the plurality of sensing vectors having the lowest determined signal difference as a first sensing vector; and
    selecting a sensing vector of the plurality of sensing vectors having the next lowest determined signal difference as a second sensing vector.

4. The method of claim 1, wherein the selection metrics include a sensing vector selection metric and a morphology selection metric, the method further comprising:
    ranking sensing vectors of the plurality of sensing vectors based on the determined sensing vector selection metric to determine a first vector ranking;
    ranking sensing vectors of the plurality of sensing vectors based on the determined morphology selection metric to determine a second vector ranking;
    comparing the first vector ranking and the second vector ranking; and updating the first vector ranking in response to the comparing.

5. The method of claim 1, further comprising:
analyzing electrical signals sensed on the selected sensing vector;
detecting tachycardia based on the analysis; and
delivering an electrical therapy to a heart in response to detecting the tachycardia.

6. A method of determining sensing vectors in a medical device, comprising:
sensing cardiac signals on a plurality of sensing vectors formed from a plurality of electrodes;
determining, for each of the sensed cardiac signals, a plurality of sensing vector metrics;
determining, for each of the sensed cardiac signals, a plurality of morphology metrics associated with a morphology;
determining, for each of the plurality of sensing vectors, selection metrics based on at least the plurality of determined sensing vector metrics and the plurality of determined morphology metrics, wherein the selection metrics include a sensing vector selection metric and a morphology selection metric; and
ranking vectors of the plurality of sensing vectors based on the determined sensing vector selection metric to determine a first vector ranking;
ranking vectors of the plurality of sensing vectors based on the determined morphology selection metric to determine a second vector ranking;
comparing the first vector ranking and the second vector ranking;
updating the first vector ranking in response to the comparing, wherein the first vector ranking comprises at least a first sensing vector, a second sensing vector and a third sensing vector and the second vector ranking comprises at least a low morphology selection metric associated with a low number of pulses, a medium morphology selection metric and a high morphology selection metric, and wherein comparing the first vector ranking and the second vector ranking comprises determining whether the second vector ranking of one of the first sensing vector and the second sensing vector corresponds to the high morphology metric; and
selecting a sensing vector of the plurality of sensing vectors based on at least one of the first or second vector rankings and at least some of the determined selection metrics.

7. The method of claim 6, wherein selecting the sensing vector comprises:
selecting the first sensing vector and the second sensing vector when neither one of the first sensing vector or the second sensing vector is determined to correspond to the high morphology selection metric; and
determining whether to select the third sensing vector when at least one of the first sensing vector or the second sensing vector is determined to correspond to the high morphology selection metric.

8. The method of claim 7, wherein determining whether to select the third sensing vector comprises:
comparing the morphology selection metric of the one of the first sensing vector and the second sensing vector determined to correspond to the high morphology selection metric and the morphology selection metric of the third sensing vector to determine a first relative difference;
comparing the vector selection metric of the one of the first sensing vector or the second sensing vector determined to correspond to the high morphology selection metric and the vector selection metric of the third sensing vector to determine a second relative difference; and
selecting the third sensing vector based on at least the first relative difference and the second relative difference.

9. The method of claim 8, further comprising:
determining whether the first relative difference is greater than a first difference threshold;
determining whether the second relative difference is less than a second difference threshold; and
updating the selected sensing vectors from the first sensing vector and the second sensing vector to the one of the first sensing vector or the second sensing vector not determined to correspond to the high morphology selection metric and the third sensing vector in response to both the first relative difference being greater than the first difference threshold and the second relative difference being less than the second difference threshold.

10. The method of claim 6, further comprising:
analyzing electrical signals sensed on the selected sensing vector;
detecting tachycardia based on the analysis; and
delivering an electrical therapy to a heart in response to detecting the tachycardia.

11. A medical device, comprising:
a plurality of electrodes capable of forming a plurality of sensing vectors for sensing cardiac signals; and
a processor configured to obtain the cardiac signals sensed via the plurality of sensing vectors, determine, for each of the plurality of sensing vectors, at least one sensing vector metric of the sensed cardiac signals, determine, for each of the plurality of sensing vectors, at least one morphology metric associated with a morphology of the sensed cardiac signals by sensing an R-wave in response to the cardiac signal exceeding a sensing threshold, determining pulses associated with the sensed R-wave, determining, for each pulse, whether a pulse width of the pulse is less than a pulse width threshold, determining, for each pulse, whether a pulse amplitude of the pulse is greater than a pulse amplitude threshold, determining a number of the determined pulses having both a pulse width less than the pulse width threshold and a pulse amplitude greater than the pulse amplitude threshold, and setting the morphology metric equal to the determined number of pulses, determine, for each of the plurality of sensing vectors, selection metrics based on at least the determined sensing vector metric and the determined morphology metric, and select a sensing vector of the plurality of sensing vectors based on at least the determined selection metrics.

12. The medical device of claim 11, wherein the processor is further configured to set a window of time determined based on the sensed R-wave, determine signal differences between the sensed cardiac signal and the sensing threshold during the window of time, and set the sensing vector metric based on at least the determined signal differences.

13. The medical device of claim 12, wherein the processor is further configured to select a sensing vector of the plurality of sensing vectors having the lowest determined signal difference as a first sensing vector, and select a sensing vector of the plurality of sensing vectors having the next lowest determined signal difference as a second sensing vector.

14. The medical device of claim 11, wherein the determined selection metrics include a sensing vector selection metric and a morphology selection metric and the processor is further configured to rank vectors of the plurality of sensing vectors based on at least the determined sensing vector selection metric to determine a first vector ranking, rank vectors of the plurality of sensing vectors based on at least the determined morphology selection metric to determine a second vector ranking, compare the first vector ranking and the second vector ranking, and update the first vector ranking based on at least the comparing.

15. The device of claim 11, wherein the processor is further configured to analyze electrical signals sensed on the selected sensing vector, detect tachycardia based on the analysis, and deliver an electrical therapy to a heart in response to detecting the tachycardia.

16. A medical device, comprising:
a plurality of electrodes capable of forming a plurality of sensing vectors for sensing cardiac signals; and
a processor configured to obtain the cardiac signals sensed via the plurality of sensing vectors, determine, for each of the sensed cardiac signals, a plurality of sensing vector metrics, determine, for each of the sensed cardiac signals, a plurality of morphology metrics associated with a morphology, determine, for each of the plurality of sensing vectors, selection metrics based on at least the plurality of determined sensing vector metrics and the plurality of determined morphology metrics, wherein the selection metrics include a sensing vector selection metric and a morphology selection metric, rank vectors of the plurality of sensing vectors based on the determined sensing vector selection metric to determine a first vector ranking, rank vectors of the plurality of sensing vectors based on the determined morphology selection metric to determine a second vector ranking, compare the first vector ranking and the second vector ranking, and update the first vector ranking in response to the comparing, wherein the first vector ranking comprises at least a first sensing vector, a second sensing vector and a third sensing vector and the second vector ranking comprises at least a low morphology selection metric associated with a low number of pulses, a medium morphology selection metric and a high morphology selection metric, and wherein the processor is further configured to determine whether the second vector ranking of one of the first sensing vector and the second sensing vector corresponds to the high morphology selection metric, and select a sensing vector of the plurality of sensing vectors based on at least one of the first or second vector rankings and at least some of the determined selection metrics.

17. The medical device of claim 16, wherein the processor is further configured to select the first sensing vector and the second sensing vector in response to neither one of the first sensing vector and the second sensing vector being determined to correspond to the high morphology selection metric, and determine whether to select the third sensing vector in response to at least one of the first sensing vector and the second sensing vector being determined to correspond to the high morphology selection metric.

18. The medical device of claim 17, wherein the processor is further configured to compare the morphology selection metric of the one of the first sensing vector and the second sensing vector determined to correspond to the high morphology selection metric and the morphology selection metric of the third sensing vector to determine a first relative difference, compare the vector selection of the one of the first sensing vector and the second sensing vector determined to correspond to the high morphology selection metric and the vector selection metric of the third sensing vector to determine a second relative difference, and select the third sensing vector in response to the first relative difference and the second relative difference.

19. The medical device of claim 18, wherein the processor is further configured to determine whether the first relative difference is greater than a first difference threshold, determine whether the second relative difference is less than a second difference threshold; and update the selected sensing vectors from the first sensing vector and the second sensing vector to the one of the first sensing vector and the second sensing vector not determined to correspond to the high morphology selection metric and the third sensing vector in response to both the first relative difference being greater than the first difference threshold and the second relative difference being less than the second difference threshold.

20. The device of claim 16, wherein the processor is further configured to analyze electrical signals sensed on the selected sensing vector, detect tachycardia based on the analysis, and deliver an electrical therapy to a heart in response to detecting the tachycardia.

21. A non-transitory, computer-readable storage medium storing instructions for causing a processor included in a medical device to perform a method for determining sensing vectors, the method comprising:
sensing cardiac signals on a plurality of sensing vectors formed from a plurality of electrodes;
determining, for each of the plurality of sensing vectors, at least one sensing vector metric of the sensed cardiac signals;
determining, for each of the plurality of sensing vectors, at least one morphology metric associated with a morphology of the sensed cardiac signals, wherein determining a morphology metric comprises:
sensing an R-wave in response to the cardiac signal exceeding a sensing threshold;
determining pulses associated with the sensed R-wave;
determining, for each pulse, whether a pulse width of the pulse is less than a pulse width threshold;
determining, for each pulse, whether a pulse amplitude of the pulse is greater than a pulse amplitude threshold;
determining a number of the determined pulses having both a pulse width less than the pulse width threshold and a pulse amplitude greater than the pulse amplitude threshold; and
setting the morphology metric equal to the determined number of pulses;
determining, for each of the plurality of sensing vectors, selection metrics based on at least the determined sensing vector metric and the determined morphology metric;
selecting a sensing vector of the plurality of sensing vectors based on at least the determined selection metrics
analyzing electrical signals sensed on the selected sensing vector;
detecting tachycardia based on the analysis; and
delivering an electrical therapy to a heart in response to detecting the tachycardia.

* * * * *